(12) United States Patent
Lee et al.

(10) Patent No.: US 8,252,337 B2
(45) Date of Patent: Aug. 28, 2012

(54) CHARGED MESOPOROUS SILICA NANOPARTICLE-BASED DRUG DELIVERY SYSTEM FOR CONTROLLED RELEASE AND ENHANCED BIOAVAILABILITY

(75) Inventors: Chia-Hung Lee, Tainan (TW); Leu-Wei Lo, Taipei (TW); Chung-Shi Yang, Taichung (TW); Chung-Yuan Mou, Taipei (TW)

(73) Assignee: National Health Research Institutes, Miaoli County (TW)

( * ) Notice: Subject to any disclaimer, the term of this patent is extended or adjusted under 35 U.S.C. 154(b) by 312 days.

(21) Appl. No.: 12/581,965

(22) Filed: Oct. 20, 2009

(65) Prior Publication Data
US 2010/0104650 A1   Apr. 29, 2010

Related U.S. Application Data (60) Provisional application No. 61/107,721, filed on Oct. 23, 2008.

(51) Int. Cl.
*A61K 9/14*  (2006.01)
*A61K 47/18* (2006.01)

(52) U.S. Cl. ......... 424/489; 514/788
(58) Field of Classification Search ......... None
See application file for complete search history.

(56) References Cited

U.S. PATENT DOCUMENTS

| | | | |
|---|---|---|---|
| 2003/0152759 A1* | 8/2003 | Chao et al. | 428/307.3 |
| 2006/0018966 A1* | 1/2006 | Lin et al. | 424/484 |
| 2007/0275068 A1 | 11/2007 | Martens et al. | |
| 2009/0192205 A1 | 7/2009 | Augustijns et al. | |
| 2009/0252811 A1 | 10/2009 | Lin et al. | |
| 2010/0303723 A1* | 12/2010 | Farokhzad et al. | 424/9.1 |

FOREIGN PATENT DOCUMENTS

JP    2004250265 A   *   9/2004

OTHER PUBLICATIONS

A raw machine translation for JP 2004/250265A has been provided.*
Walcarius, A.; Ganesan, V. Ion-Exchange Properties and Electrochemical Characterization of Quaternary Ammonium-Functionalized Silica Micropsheres Obtained by the Surfactant Template Route. Langmuir 2006, 22, 469-477.*
http://www.merriam-webster.com/dictionary/nanoparticle as referenced on Jun. 7, 2012.*
Vinu, A; Hossain, K.Z.; Ariga, K. Recent Advances in Functionalization of Mesoporous Silica. Journal of Nanoscience and Nanotechnology, vol. 5, p. 347-371, 2005.*
Lee, C. H.; Lo, L. W.; Mou, C. Y., Yang, C. S. (2008) Synthesis and characterization of positive-charge functionalized mesoporous silica nanoparticles for the controlled release of anionic molecules, Adv Funct Mater 18:3283-3292.

* cited by examiner

*Primary Examiner* — Robert A Wax
*Assistant Examiner* — Jessica Worsham
(74) *Attorney, Agent, or Firm* — Hsiu-Ming Saunders; Intellectual Property Connections, Inc.

(57) ABSTRACT

A charged mesoporous silica nanoparticle (MSN)-based drug delivery system for controlled release and enhanced bioavailability is disclosed. The system comprises a positively charged MSN, which has a silica matrix and an array of pores and/or nanochannels in the matrix. The entire substance of the matrix, all the surfaces and the pores and/or nanochannels comprise a plurality of silanol (Si—OH) and quaternary ammonium functional groups. The bioavailability of a negatively charged bioactive compound can be increased by loading it into the pores and/or nanochannels. The silanol (Si—OH) functional groups on the surfaces lining the walls of the pores and/or nanochannels are free to deprotonate in a fluid having pH above the pI of the positively charged MSN and lead to a sustained release of the negatively charged drug from the pores and/or nanochannels, and thereby enhance the bioavailability of the drug.

19 Claims, 10 Drawing Sheets

CHARGED MESOPOROUS SILICA NANOPARTICLE-BASED DRUG DELIVERY SYSTEM FOR CONTROLLED RELEASE AND ENHANCED BIOAVAILABILITY

REFERENCE TO RELATED APPLICATION

The present application claims the priority to U.S. Provisional Application Ser. No. 61/107,721, filed Oct. 23, 2008, which is herein incorporated by reference in its entirety.

FIELD OF THE INVENTION

The present invention relates generally to a drug delivery system, and more specifically to a controlled release and enhanced bioavailability drug delivery system.

BACKGROUND OF THE INVENTION

There are still many challenges in designing drug delivery systems for treating colon-related diseases such as irritable bowel syndrome, Crohn's disease and ulcerative colitis. To ensure its delivery to the colon tissue, an oral drug needs to be formulated to be resistant to stomach acid and minimize intestinal release before it reaches the colon. The major formulations of colonic drug delivery systems developed during the past decade have been based on time-dependent release, pH-sensitive polymer coatings, and prodrug systems.

The time-dependent-release formulation is designed to delay the onset of the drug release until it reaches the colon. This kind of formulation suffers from the disadvantage that a precise control of colon site-specific release is not easy to achieve because the transit time from the mouth to the colon is variable. The pH-dependent release formulation is based on the different pH values in various segments of the GI tract. This kind of formulation has the disadvantage that the drug, although successfully passing through the stomach, is prematurely released in the small intestine because the pH of the small intestine and colon are not significantly different. The prodrug formulation is based on the presence of bacteria in the colon (about $10^{12}$ CFU/mL), which catalyze reactions that convert a prodrug into an active drug. This strategy suffers from the disadvantage that a portion of the prodrug is converted into the active form in the stomach and small intestine, which contain lower amounts of the same bacteria (about $10^4$ CFU/mL).

Mesoporous silica nanoparticles (MSN) have been used to incorporate large dosages of hydrophobic drugs inside their nanochannels. They have also been used to incorporate a contrast agent for in vivo cell tracking purposes. Although MSN are useful in carrying drug molecules, its loading capacity and use for controlled drug release have been a challenge for developing good bioavailability and site-specific drug delivery system.

A previously unaddressed need exists in the art to address the deficiencies and inadequacies, especially in connection with establishment of a good bioavailability and controlled release drug delivery system.

SUMMARY OF THE INVENTION

In one aspect, the invention relates to a composition having a positively charged mesoporous silica nanoparticle (MSN), which comprises:
(a) a silica matrix, the entire substance of which comprises a plurality of silanol (Si—OH) and quaternary ammonium functional groups; and
(b) an array of pores and/or nanochannels in the matrix, each pore and/or nanochannel having a surface lining the wall thereof;
wherein the surface lining the wall of each pore and/or nanochannel comprises a plurality of silanol (Si—OH) and quaternary ammonium functional groups.

In one embodiment of the invention, the entire silica matrix comprises a copolymer of a silicate precursor and an organosilane quaternary ammonium compound.

In one embodiment of the invention, the organosilane quaternary ammonium compound comprises the formula:

(II)

wherein $R_1$, $R_2$, $R_3$, $R_4$, $R_5$, $R_6$, $R_7$ and R are the same or different; $R_1$, $R_2$, $R_3$ are, independently of each other, selected from the group consisting of alkyl and alkene groups; $R_4$, $R_5$, $R_6$, $R_7$ and $R_8$ are, independently of each other, selected from the group consisting of alkyl, ammonium, and hydrogen; n is an integer and $20 \geq n \geq 1$. Preferably, the alkyl is $C_{1-6}$ alkyl, and the alkene is $C_{1-6}$ alkene.

In one embodiment of the invention, the quaternary ammonium silane is selected from the group consisting of N-trimethoxysilylpropyl-N,N,N-trimethylammonium chloride and N-trimethoxysilylpropyl-N,N,N-triethylammonium chloride.

In another embodiment of the invention, each pore and/or nanochannel comprises no oxysilyl functional groups (—O—Si) extending into the space inside the pore or nanochannel.

In another embodiment of the invention, the silicate precursor is selected from the group consisting of sodium silicate and a compound of the formula:

(I)

wherein $R'_1$, $R'_2$, $R'_3$ and $R'_4$ are the same or different, and represent, independently of each other, an alkyl or an aryl group.

In one embodiment, $R'_1$, $R'_2$, $R'_2$, $R'_3$ and $R'_4$ are $C_{1-6}$ alkyl or $C_{1-6}$ aryl.

In another embodiment of the invention, the silicate precursor is at least one selected from the group consisting of tetraethoxysilane (TEOS), tetramethoxysilane (TMOS), and sodium silicate.

In another embodiment of the invention, the plurality of silanol (Si—OH) functional groups on the surfaces lining the walls of the pores and/or nanochannels are provided by a silicate precursor that is incorporated into the matrix, and are free to deprotonate or to protonate, respectively, in a fluid having pH above or below the isoelectric point (pI) of the positively charged MSN.

In another embodiment of the invention, the aforementioned composition further comprises a plurality of negatively charged bioactive compound molecules adsorbed onto the surfaces lining the pores and/or nanochannels. The negatively charged bioactive compound molecules are attracted onto the quaternary ammonium functional groups on the surfaces lining the pores and/or nanochannels.

In another embodiment of the invention, the bioactive compound is at least one selected from the group consisting of sulfa drugs, 5-aminosalicylic acid, aspirin, methotrexate, alendronate, ibuprofen, and amoxicillin.

In another embodiment of the invention, the bioactive compound is an acidic, anionic compound.

In another embodiment of the invention, the plurality of silanol (Si—OH) functional groups on the surfaces lining the walls of pores and/or nanochannels are mostly in a protonated state.

In another embodiment of the invention, the plurality of silanol (Si—OH) functional groups on the surfaces lining the walls of the pores and/or nanochannels are provided by a silicate precursor that is incorporated into the matrix, and are free to deprotonate or to protonate, respectively, in a fluid having pH above or below the isoelectric point (pI) of the positively charged MSN.

Further in another aspect, the invention relates to a method of preparing the aforementioned composition. The method comprises the steps of
  (a) admixing a silicate precursor with a surfactant in the presence of a catalyst to form a crystal seed in a suspension;
  (b) adding an organosilane quaternary ammonium compound and an additional amount of the silicate precursor into the suspension from step (a) to form a silica matrix; and
  (c) extracting the silica matrix with a solvent to remove the surfactant and thereby obtain the composition.

The catalyst may be a base catalyst including, but not limited to, $NH_4OH$, NaOH, trimethylamine, and triethylamine. Alternatively, the catalyst may be an acid catalyst.

The surfactant may be a cationic or a nonionic surfactant. A cationic surfactant may comprise the formula: $CH_3(CH_2)_nN(X)(CH_3)_3$ wherein X is Cl or Br; n is an integer from 11 to 20. In one embodiment of the invention, the surfactant is cetyltrimethylammonium bromide (CTAB).

A nonionic surfactant may be a polymer comprising the formula PEG-PPG-PEG [Poly(ethylene glycol)-block-poly(propylene glycol)-block-poly(ethylene glycol)]. The nonionic polymer surfactant may be selected from the group consisting of EO20PO70EO20 (Pluronic® P-123), EO106PO70EO106 (Pluronic® P-127), and EO132PO50EO132 (Pluronic® P-108).

The solvent used to extract MSN and to remove the surfactant template may be an alcohol containing an acid, such as HCl, or a salt, such as NH4NO3, to facilitate the breaking down of the interaction between the surfactant template and the wall lining the pores and/or nanochannels.

In another aspect, the invention relates to a method for preparing a colonic drug-sustained-release system. The method comprises the steps of
  (a) providing a composition according to claim 1; and
  (b) loading a plurality of negatively charged bioactive compound molecules into the pores and/or nanochannels to obtain the colonic drug-sustained-release system.

Further in another aspect, the invention relates to a method for enhancing the bioavailability of a negatively charged drug. The method comprises the steps of:

(a) providing a composition as aforementioned; and
  (b) loading a plurality of negatively charged drug molecules into the pores and/or nanochannels of the positively charged MSN to obtain a composition comprising a MSN absorbed with the plurality of drug molecules and thereby enhancing the bioavailability of the negatively charged drug.

In another embodiment of the invention, the plurality of silanol (Si—OH) functional groups on the surfaces lining the walls of the pores and/or nanochannels are free to deprotonate in a fluid having pH above the pI of the positively charged MSN and lead to a sustained release of the negatively charged drug from the pores and/or nanochannels, and thereby enhance the bioavailability of the negatively charged drug.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

Charge density: The electric charge per unit area or per unit volume of a body or of a region of space.

As used herein, "adsorption" shall generally mean the accumulation of atoms or molecules on the surface of a material.

As used herein, "desorption" shall generally mean a phenomenon whereby a substance is released from or through a surface. The process is the opposite of sorption.

As used herein, the "isoelectric point" is the pH at which a particular molecule or surface carries no net electrical charge.

As used herein, the term "in vivo" means within a living organism; occurring or made to occur within a living organism.

As used herein, the term "anionic compound" is one that contains a full negative charge.

As used herein, the terms "matrix" and "framework" are interchangeable.

As used herein, "MSN-TA" shall generally mean a mesoporous silica nanoparticle that has been modified by trimethylammonium (TA) functional groups. The TA functional groups are incorporated into the matrix (and/or framework) of MSN via a co-condensation method.

The full names for abbreviations used herein are as follows: MSN for mesoporous silica nanoparticles, TA for trimethylammonium, TEOS for tetraethoxysilane, CTAB for cetyltrimethylammonium bromide, P-MSN for pure form MSN.

Figure 1A:
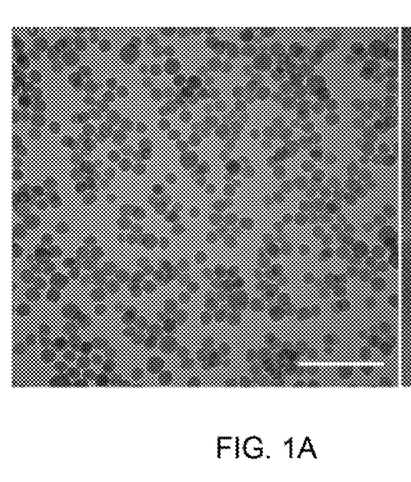
FIGS. 1A-1B show transmission electron microscopy images of MSN-TA samples. Scale bars: 500 nm (A) and 20 nm (B).
Figure 1B:
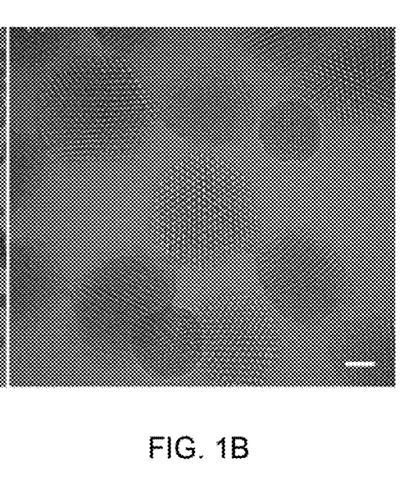
Figure 1C:
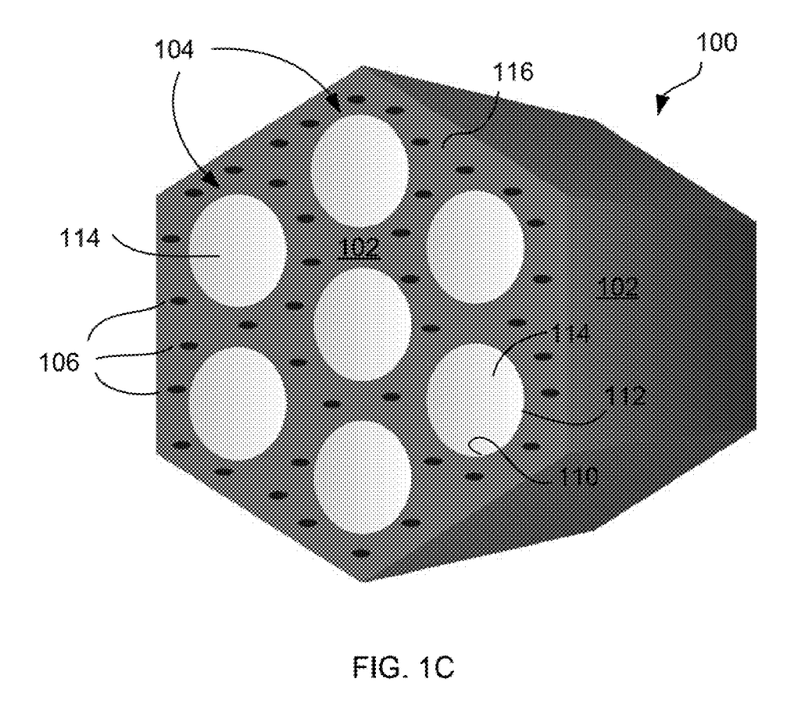
FIG. 1C is a schematic drawing showing an MSN-TA sample.

The invention relates to a positively charged mesoporous silica nanoparticle (MSN) 100 composed of a silica matrix 102 and an array of pores and/or nanochannels 104 in the matrix 102 (FIG. 1C). Each pore and/or nanochannel 104 has a surface 110 lining the wall 112 of the pore and/or nanochannel 104. Both the matrix substance 102, all the surfaces 116 and inside the pores 114 comprise a plurality of quaternary ammonium 106 and silanol (Si—OH) 108 functional groups. The inset 142 in FIG. 1E shows the surface 110 lining the wall 112 of the pore 104 comprises a plurality of silanol (Si—OH) 108 and quaternary ammonium 106 functional groups. The bioavailability of a drug can be increased by loading it into the pores 104. The entire matrix 102, all the surfaces 116, and the surfaces lining the walls of the pores 110 all comprise quaternary ammonium functional groups 106 (FIG. 1C).

Figure 1D:
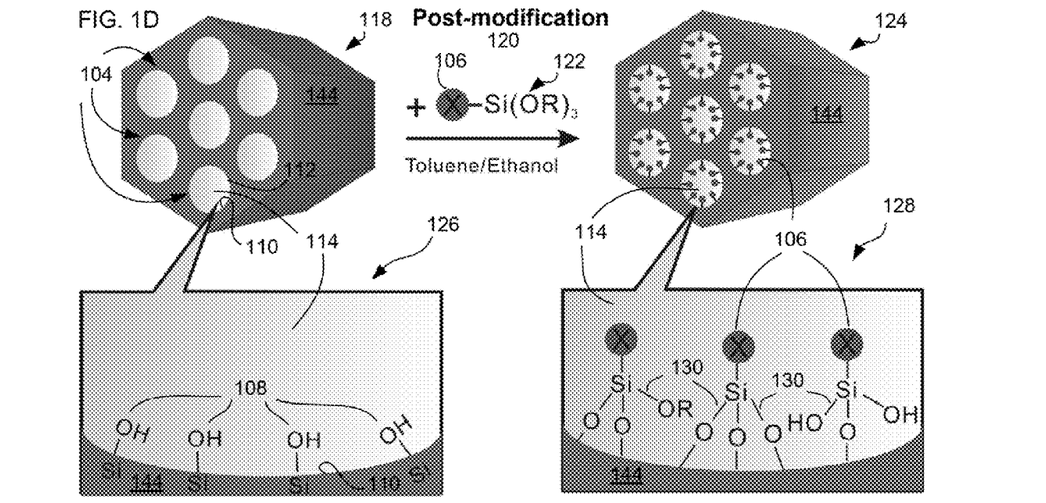
FIG. 1D is a schematic drawing showing synthesis of a surface-modified MSN by post-modification.
Figure 1E:
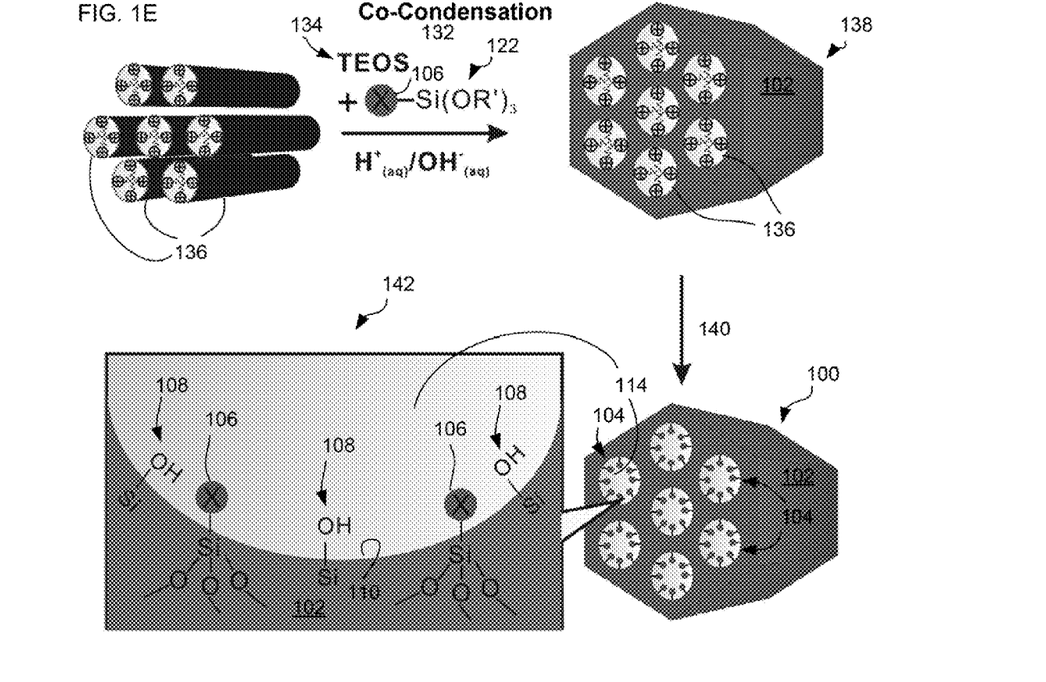
FIG. 1E is a schematic drawing showing synthesis of a surface-modified MSN by co-condensation.

As illustrated in FIG. 1D, a MSN with surfaces modified with positively charges 124 may be synthesized by post-modification 120. This method modifies the surfaces of MSN 118 with an organosilane quaternary ammonium compound 122 after a template is removed. A condesation reaction occurs between the quaternary ammonium organosilane (e.g., methoxysilane) 122 and the silanol (Si—OH) 108 functional groups on the surfaces of MSN 118. Such a surface modification uses and leads to a reduction in the surface silanol groups. The inset 126 shows an enlarged portion of the inside of a pore/nanochannel 114 of a MSN 118 before surface modification, in which the surface 110 lining the wall 112 of each pore and/or nanochannel 114 comprises a plurality of silanol (Si—OH) functional groups 108. An organosilane quaternary ammonium compound 122 comprising a quaternary ammonium functional group 106 (in FIG. 1D, where the circled X represents "trimethylammonium" functional group) is used to modify the surfaces of mesoporous silica 118 to obtain a surface-modified mesoporous silica 124. The inset 128 shows an enlarged portion of the inside of the pore/nanochannel 114 of a post-modification-synthesized MSN 124. It shows the surface Silanol (Si—OH) groups are reduced because they were used to condense with quaternary ammonium organosilane 122. The post-modification method 120 resulted in a positively charged MSN 124 that has oxysilyl (O—Si) functional groups 130 extending into the space inside the pores and/or nanochannel 114. In addition, because only the surfaces are modified, the matrix substance 144 is not modified and thus does not contain quaternary ammonium functional groups.

Another way to synthesize a MSN with surfaces modified with positively charges is by co-condensation 132. During the process of hydrolyzation and polymerization of a silicate precursor 134, e.g., TEOS or sodium silicate, in the presence of a template (e.g., CTAB) 136, an organosilane quaternary ammonium compound 122 comprising a quaternary ammonium functional group 106 is added so that the hydrolyzed silicate products copolymerize with the quaternary ammonium organosilane 122 to generate an initial silica product 138, which is extracted by acidic alcohol 140. The template 136 is later removed to generate positively charged MSN 100. The co-condensation method 132 resulted in a positively charged MSN 100 that does not have the oxysilyl (O—Si) functional groups 130 extending into the space inside the pores and/or nanochannels like the one synthesized by post-modification does. The inset 142 shows an enlarged portion of the inside of the pore/nanochannel 114 of the co-condensation-synthesized positively charged MSN 100.

Figure 11:
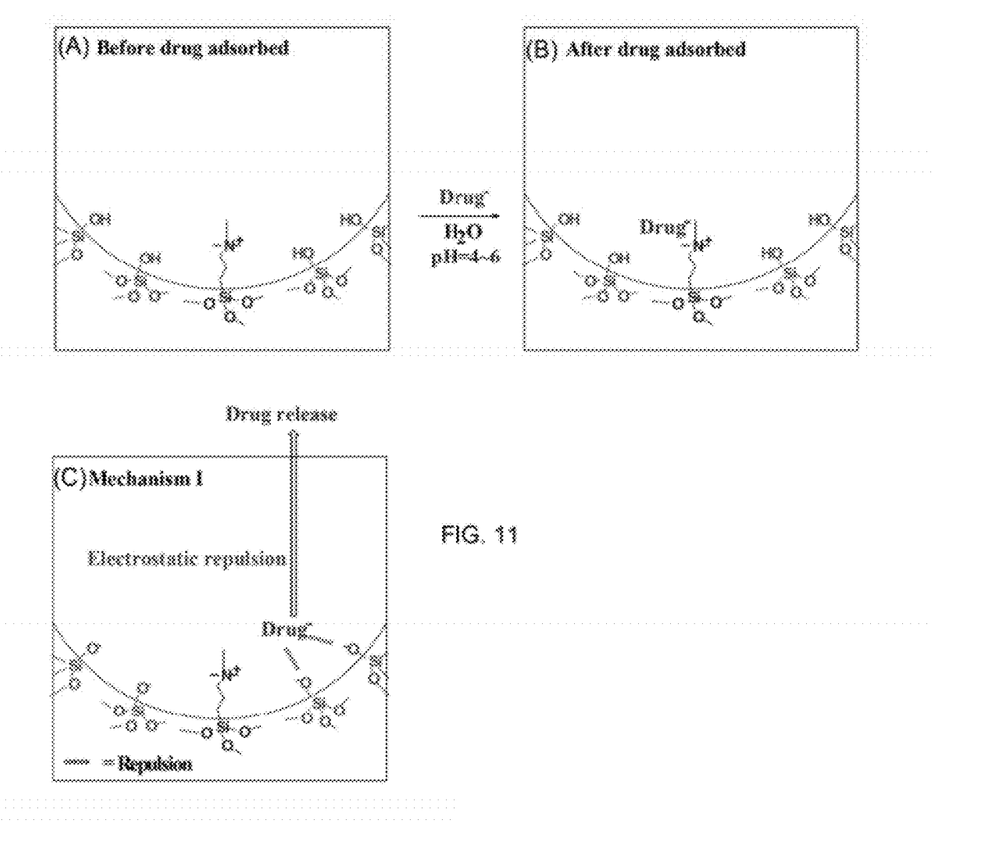
FIG. 11 is a schematic representation of a sustained-release mechanism of an anionic drug adsorbed onto MSN-TA sample. (A): before drug is adsorbed; (B): after drug is adsorbed; (C): drug released by electrostatic repulsion under a neutral pH.

Although both methods can synthesize a surface-modified MSN, the resulted products differ significantly in structure and physicochemical properties. A surface-modified MSN synthesized by the post-modification method lacks effective functional groups for controlling drug release. Its ability in controlling drug release under different pH is often very poor. In contrast, a surface-modified MSN synthesized by the co-condensation method comprises two kinds of functional groups, quaternary ammonium and silanol (Si—OH) (FIGS. 1E and 11A). The quaternary ammonium functional groups are used to increase the loading capacity for a negatively charged drug (FIG. 11B). The silanol (Si—OH) functional group becomes negatively charged at neutral pH. This leads to electrostatic repulsion of the negatively charged drug, and facilitates drug release (FIG. 11C).

Bioactive compounds that are suitable for loading into the positively charged MSNs are drugs effective for treating diseases afflicted in the lower part of the gastrointestinal tract. These disease include, but not limited to, Crohn disease, ulcerative colitis, irritable colitis, and colic cancer. These drugs include, but are not limited to, sulfasalazine (an anti-inflammatory pro-drug for bowl disease), 5-aminosalicylic acid (an anti-inflammatory drug for Crohn's disease), aspirin (an antithrombotic drug), methotrexate (an anticancer drug), alendronate (antiosteoporosis drug), ibuprofen (Non-steroidal anti-inflammatory drug), and amoxicillin (β-lactam antibiotic drug).

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Preparation of Positive-Charged MSN

The following materials were purchased from Across: TEOS, CTAB, Orange II and ammonium hydroxide (30%). Sulfasalazine was obtained from Sigma Chemical Co. N-Trimethoxysilylpropyl-N,N,N-trimethylammonium chloride (50% in methanol) was obtained from Gelest. Ringer's solution has a composition very similar to human plasma (NaCl, 8.60 mg; KCl, 0.3 mg; $CaCl_2$, 0.33 mg per mL of H2O).

MSN-TA Samples were prepared according to the methods as previously described. (Lee et al. 2008) "Synthesis and characterization of positive-charge functionalized mesoporous silica nanoparticles for oral drug delivery of an anti-inflammatory drug" Adv. Funct. Mater. 18:1-10, which is herein incorporated by reference in its entirety). Briefly, various MSN-TA samples with an ordered hexagonal pore structure were synthesized under a low concentration of TEOS, surfactant (CTAB), and a base catalyst ($NH_4OH$) in a two-step preparation. The low concentration of the silica precursor TEOS served as a crystal seed. The sol-gel process for the co-condensation of TEOS and N-trimethoxysilylpropyl-N,N,N-trimethylammonium chloride to synthesize the MSN-TA samples was as follows. First, 0.1 g of the template CTAB was dissolved in 50 g of 0.51 M $NH_4OH$ at 50° C., followed by addition of 0.8 mL of 0.2M dilute TEOS (in ethanol) with vigorous stirring. After the solution was stirred for 5 h to form narrow crystal seeds, 0.8 mL of ethanol containing various concentrations (2%, 5%, 8% and 12% v/v) of N-trimethoxysilylpropyl-N,N,N-trimethylammonium chloride and 0.8 mL of 1.0M TEOS were added with vigorous stirring for another 1 h to obtain the polymer. The solution was then aged without stirring at 50° C. for 24 h to obtain stable crystal particles and evaporated part of $H_2O$. Samples were collected by centrifugation at 12 000 rpm for 20 min, washed, and redispersed with deionized water and ethanol several times. The solid products were obtained by centrifugation. The surfactant templates were removed by extraction in acidic ethanol (about 0.17 g of HCl in 9 mL of ethanol at 65° C. for 24 h). The MSN-TA samples synthesized from reactions containing 2%, 5%, 8% and 12% (v/v) of N-trimethoxysilylpropyl-N,N,N-trimethylammonium chloride were designated MSN-TA-1, MSN-TA-2, MSN-TA-3 and MSN-TA-4, respectively.

Example 2

Preparation of Drug-Loaded MSN

Orange II-Loaded MSN-TA Samples: Orange II was dissolved in $H_2O$ at concentrations of 0.25, 0.75, 1.25, 1.75, 2.25 and 2.75 mM, and the pH was adjusted to 6.8 with NaOH or HCl solution. About 15 mg of MSN-TA sample was added to 2.5 mL of Orange II solution and stirred for 2 h at 30° C. The particles were washed with deionized water and centrifuged for 20 min at 12 000 rpm. The supernatant was diluted 50 times with deionized water and analyzed with a UV-Vis spectrometer. The amount of Orange II adsorbed onto nanoparticles was determined by measuring the decrease in the absorption at 480 nm. Calibration experiments were performed separately before each measurement of Orange II at different concentrations. The loading percentage of Orange II onto MSN-TA-4 was about 5.9% w/w.

Sulfasalazine-Loaded MSN-TA Samples: A saturated aqueous sulfasalazine solution was prepared by dissolving 0.5 g of sulfasalazine in 1 L of $H_2O$, stirred for 6 h, and filtered through a 0.45 mm cellulose acetate membrane to remove the residual solids. The saturated sulfasalazine solution had a concentration of about 75 mM and pH at 5.4. Sulfasalazine was adsorbed onto MSN-TA samples by adding 10 mg of MSN-TA samples into 10 mL of the above saturated sulfasalazine solution. The mixture was stirred at 800 rpm for 4 h. The particles were then washed with deionized water and centrifuged for 20 min at 12 000 rpm. The supernatant was analyzed with a UV-Vis spectrometer. The amount of Sulfasalazine adsorbed onto nanoparticles was determined by measuring the decrease in absorption at 360 nm. The loading percentage of sulfasalazine onto MSN-TA-4 was about 1.7%.

Loading Sulfasalazine onto MSN-TA Samples in DMSO: The loading of sulfasalazine was increased by dissolving it in DMSO. Twenty milligrams of MSN-TA were added to 1.5 mL of 10 mM sulfasalazine in DMSO. The mixture was stirred at 800 rpm for 4 h. The particles were then washed with DMSO and centrifuged for 20 min at 12000 rpm. The supernatant was analyzed with a UV-Vis spectrometer. The loading percentage of sulfasalazine onto MSN-TA-4 was about 4.1%.

In Vitro Release Studies: In vitro release experiments were performed in simulated gastric fluid (0.1 M HCl, pH 1.2) and intestinal fluid (Ringer's solution, pH 7.4) to mimic Orange II and sulfasalazine release in the stomach and colon. Briefly, 20 mg of dye- or drug-adsorbed MSN TA samples was added to 5 mL of the simulated fluid kept at 37° C. with constant stirring at 100 rpm. The mixture was centrifuged for 20 min at 12 000 rpm and the supernatant removed for release analysis. An equal volume of fresh simulated fluid was added to the solid particles to replenish the supernatant removed, and the mixture was subsequently subjected to release analysis as aforementioned at regular intervals.

Characterization: The surface area, pore size, and pore volume were determined by N2 adsorption-desorption isotherms obtained at 77K on a Micrometric ASAP 2010 apparatus. The sample was outgassed at $10^{-3}$ Torr and 120° C. for about 3 h prior to the adsorption experiment. The pore size distribution curves were obtained from the analysis of the adsorption portion of the isotherms using the BJH (Barrett-Joyner-Halenda) method. UV-Vis spectra were taken on a Hitachi U-3010 spectrophotometer. The absorptions for Orange II and sulfasalazine were separately collected at 480 and 360 nm, respectively, and compared to standards. FTIR spectra were recorded on a Nicolet 550 spectrometer with a KBr pellet. About 1 mg of sample was mixed with 300 mg of dried KBr and then pressed. The structures of MSN-TA samples were analyzed by powder X-ray diffraction (XRD) with a Scintag X1 diffractometer using copper Ka radiation at $\lambda$=0.154 nm. The $\zeta$-potentials of pure form MSN (P-MSN) and MSN-TA samples were measured in a Malvern Nano-HT Zetasizer. Zeta potential distribution was obtained by the average of ten measurements. The samples were prepared in the concentration of 2 mg in 1 mL of ddH2O. Different pH values were adjusted by the addition of 0.02M HCl or NaOH. Before measurement, each sample was ultrasonicated for 5 min to prevent any aggregation.

Example 3

Characteristics of Positive-Charged MSN
TEM

Figure 2:
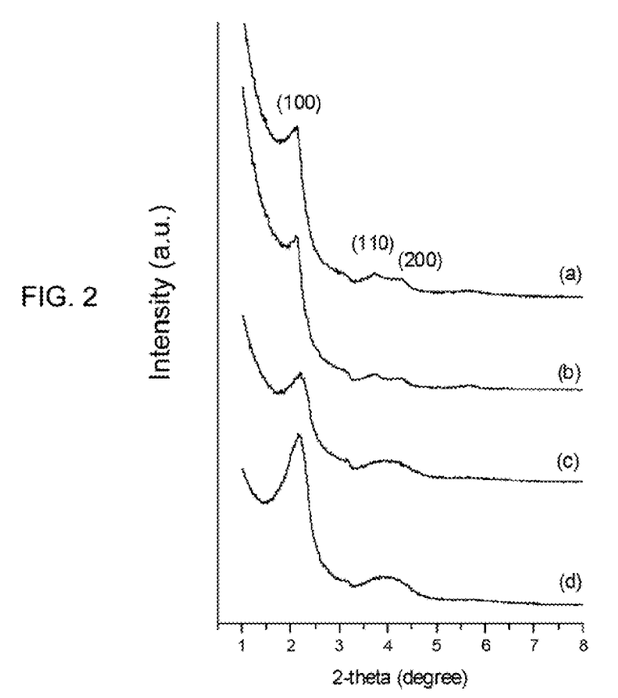
FIG. 2 shows X-ray powder diffraction spectra of (a) MSN-TA-1, (b) MSN-TA-2, (c) MSN-TA-3, and (d) MSN-TA-4 samples.
Figure 3:
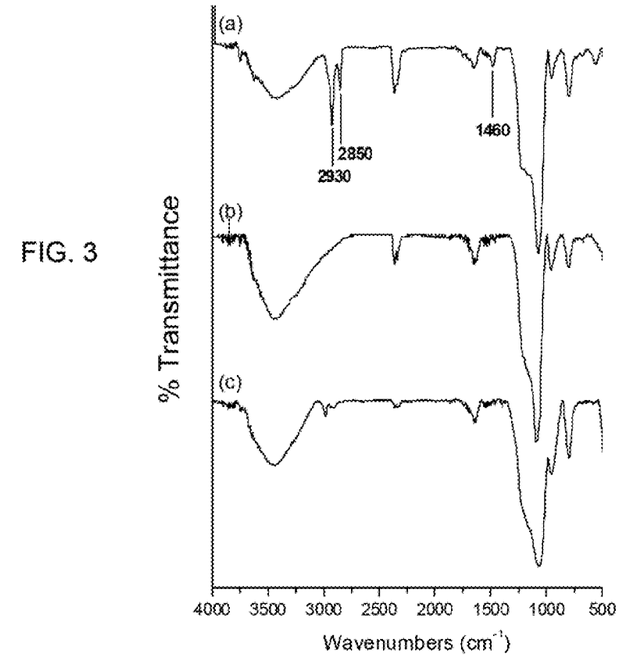
FIG. 3 shows FT-IR spectra of (a) P-MSN before extraction, (b) P-MSN after extraction, and (c) MSN-TA-4 after extraction with HCl-EtOH.
Figure 4:
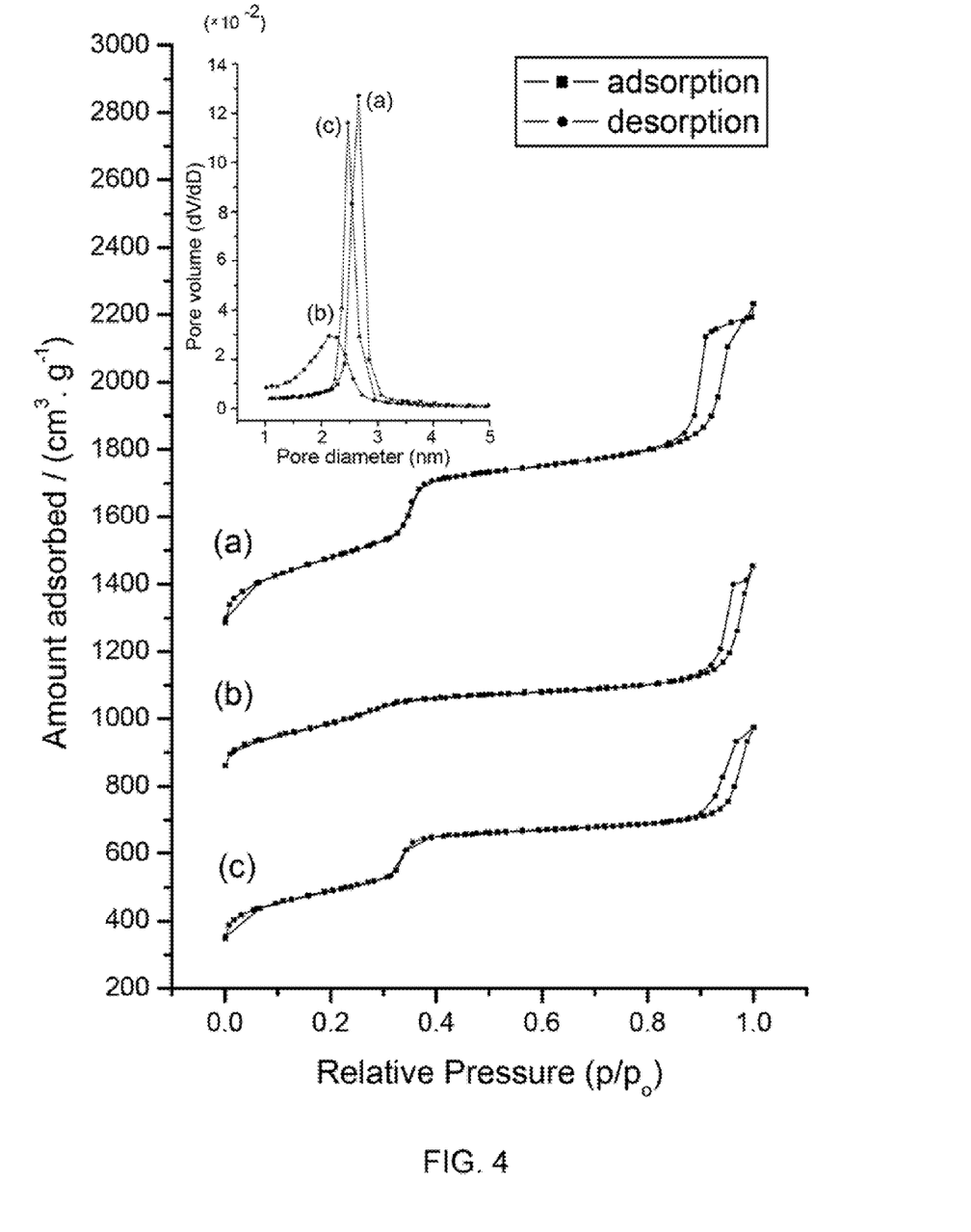
FIG. 4 shows Nitrogen adsorption-desorption isotherms and pore size distribution of MSN-TA-3 sample (a) without loading molecule, (b) after Orange II adsorption (133 mmol $g^{-1}$), and (c) after sulfasalazine adsorption (88 mmol $g^{-1}$). The inset shows pore volume versus pore diameter curves.

FIGS. 1A-1B show TEM micrographs of the TA groups-functionalized MSNs (i.e., MSN-TA). The nanochannels were hexagonal in arrangement (FIG. 1B). The MSN-TA samples have a uniform size, with an average particle diameter of about 100 nm (FIGS. 1A-1B). Conjugation of TA functional groups onto the MSN samples did not appear to affect the MSN's size (data not shown). These results indicated that the different density of the organic functional groups in MSN can be easily controlled and optimized by the sol-gel co-condensation process.
Powder XRD FIG. 2 shows the X-ray diffraction (XRD) patterns of the MSN-TA samples: (a) MSN-TA-1, (b) MSN-TA-2, (c) MSN-TA-3, and (d) MSN-TA-4. All the samples exhibit a hexagonal mesoporous structure, which is typical of MCM-41 type with (100), (110), and (200) reflections of P6 mm symmetry. As the amounts of the TA groups in the MSN-TA increased, the XRD patterns showed gradual broadening, indicating a decrease in the order of the structure. This suggested that the conjugation with an increased number of the TA functional groups had changed the pore structure of the MSN from 2-D hexagonal, ordered pores to wormlike pores. The optimum condition was 2-12% v/v of TA-silane, which resulted in MSN-TA samples with an ordered pore structure, large surface area, suitable positive charge, and a defined size.
FTIR Spectra IR spectra were employed to study the presence of organic side groups in the framework of MSN. FIG. 3(a) shows the IR spectrum of the HCl-extracted MSN without TA-modification (i.e., P-MSN). Before the extraction, a large amount of surfactant present in the sample gave the characteristic C—H valence bands at 2850-2930 $cm^{-1}$ and C—H deformation bands around 1460 $cm^{-1}$ due to the presence of the surfactant CTAB molecules. After the extraction, the complete removal of the surfactant was confirmed by the fact that these (C—H) peaks from the CTAB molecules all disappeared (FIG. 3(b)). However, the TA modified MSN (MSN-TA-4) showed the presence of (C—H) mode at 2850-2930 $cm^1$ after the HCl—EtOH extraction (FIG. 3(c)). The results indicated that the TA groups had indeed modified MSN by covalent bonding during the one-step solgel process.
Nitrogen Adsorption Studies FIG. 4 shows Nitrogen adsorption-desorption isotherms and pore-size distribution of MSN before and after the loading of Orange II (133 $\mu$mol $g^{-1}$ of MSN-TA) and sulfasalazine (88 $\mu$mol $g^{-1}$ of MSN-TA). The amounts of nitrogen adsorbed decreased with increasing amounts of loaded compounds (data not shown), primarily because the channels were occupied by the dye/drug molecules, leaving less space for nitrogen adsorption. Table 1 shows surface area, pore size, pore volume and adsorbed amounts of P-MSN and MSN-TAs. The pore size of MSN-TA-3 decreased from 27 to 22 Å when loaded with Orange II, and to 24 Å when loaded with sulfasalazine. The pore volume decreased from 1.000 to 0.505 and 0.628 cm3 $g^{-1}$, and the surface area from 1033 to 690 and 707 m2 $g^{-1}$ after being loaded with Orange II and sulfasalazine, respectively. A portion of decrease in the surface area and pore volume, as well as a shift of the average pore size from 27 to 22 and 24 Å indicated that the dye/drug molecules inside the nanochannels only partially occupied the pore space, so that there was still some room for $N_2$ adsorption. These results also provided additional evidence that the dye/drug molecules were indeed adsorbed in the nanochannels of MSN-TA samples.

TABLE 1

| Sample | TA-silane Added ($\mu$L) per mL of EtOH | Surface area ($m^2/g$) | Pore size (Å) | Pore volume ($cm^3/g$) | Orange II adsorbed ($\mu$mol/g) | Sulfasalazine adsorbed ($\mu$mol/g) | |
|---|---|---|---|---|---|---|---|
| | | | | | | $H_2O^a$ | $DMSO^b$ |
| P-MSN | 0 | 1022 | 27 | 0.969 | 17.4 | 0.5 | 4.7 |
| MSN-TA-1 | 20 $\mu$L | 1004 | 27 | 0.967 | 70.9 | 10.1 | 59.6 |
| MSN-TA-2 | 50 $\mu$L | 1081 | 27 | 1.027 | 99.6 | 20.7 | 74.2 |
| MSN-TA-3 | 80 $\mu$L | 1033 | 27 | 1.000 | 132.9 | 28.2 | 87.5 |
| MSN-TA-4 | 120 $\mu$L | 1026 | 27 | 0.968 | 167.8 | 42.8 | 103.1 |

$^a$sulfasalazine was adsorbed in an aqueous solution.
$^b$sulfasalazine was adsorbed in DMSO.

Zeta-Potential Analysis

Figure 5:
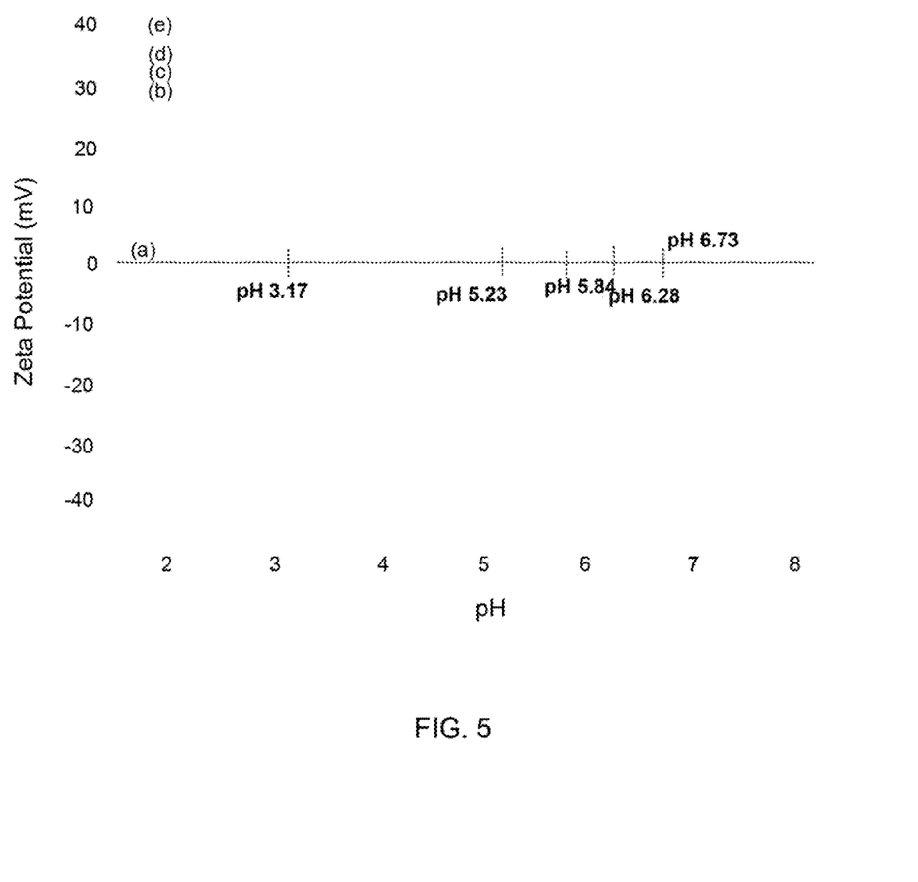
FIG. 5 shows zeta potential versus pH curves and isoelectric points of (a) pure MSN, (b) MSN-TA-1, (c) MSN-TA-2, (d) MSN-TA-3 and (e) MSN-TA-4.

The $\zeta$-potential of P-MSN and MSN-TA samples were measured in solutions with the pH ranging from 2 to 8 by automatic titration (FIG. 5). At pH 2.0, all the MSN samples showed the positive z-potential values, either when being conjugated with TA groups (MSN-TA-1, +30.3; TA-2, +32.1; TA-3, +33.7; TA-4, +39.4 mV) or without TA groups (P-MSN: +2.0 mV). We observed that the positive charge densities (from z-potential measurements) were directly related to the number of TA groups on the MSN samples. This phenomenon provided additional evidence that different TA densities were indeed modified in the framework of MSN by the sol gel process. When the pH was raised to 7.4, the silanol groups on the surface became deprotonated, and thus all of the MSN samples thus exhibited negative z-potential values (P-MSN, −40.6; MSN-TA-1, −35.1; TA-2, −28.8; TA-3, −22.2; TA-4, −11.7 mV). These results suggested that we could manipulate the TA (positive) density in the framework of MSN to optimize the loading capacity. Negatively charged drug molecules were loaded onto MSN when solution was under acidic condition (pH 4-6) since the MSN surface was covered by partial positive charges. When the solution's pH was increased to 7.4, a strong electrostatic repulsion was generated between the surface of MSN and the negative dye/drug molecules, which triggered their pH-dependent release. In addition, an increased number of the TA groups also increased the pH values for the MSN samples to reach the point of zero charge (PZC) (P-MSN, 3.17; MSN-TA-1, 5.23; TA-2, 5.84; TA-3, 6.28; TA-4, 6.73). The pH values for PZC marked the onset of the release of drugs loaded onto the MSN-TA samples. When the solution's pH value was higher than PZC, the drugs was released in a sustained manner. The pH increases from pH 1.0-3.0 in the stomach to pH 6.5-7.0 in the small intestine and finally to pH 7.0-8.0 in the colon. The difference in the PZC of the MSN-TA samples can allow the association and dissociation of loaded drugs, depending on the varied pH in the GI tract.

Example 4

Effects of Dye/Drug Concentrations on the Adsorption Efficiency

Figure 6:
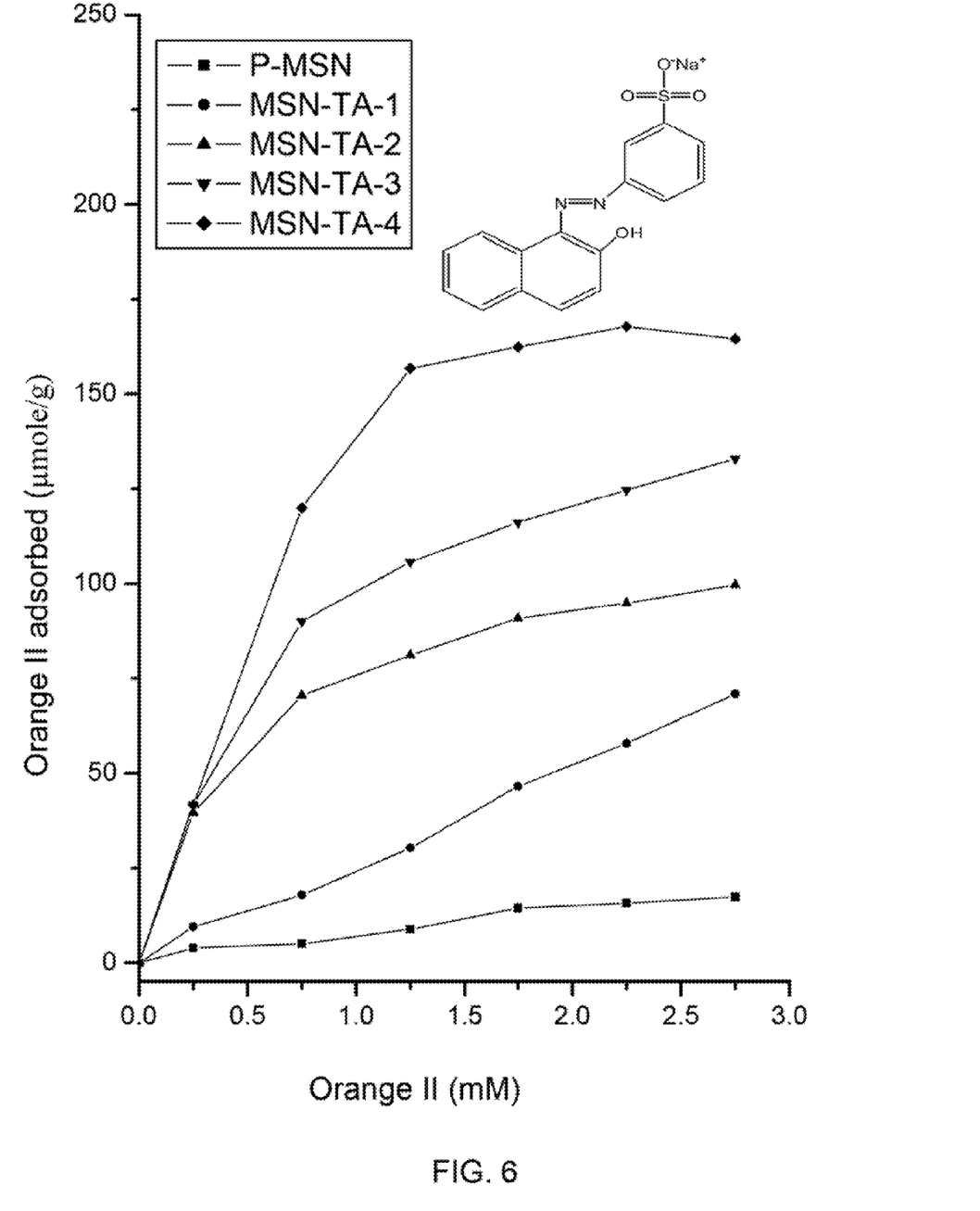
FIG. 6 shows Orange II concentration versus adsorption curves for pure MSN (square), MSN-TA-1 (solid circle), MSN-TA-2 (solid triangle), MSN-TA-3 (solid, reverse triangle) and MSN-TA-4 (solid diamond).

The effects of various initial dye/drug concentrations (Orange II: 0.25, 0.75, 1.25, 1.75, 2.25, and 2.75 mM; and sulfasalazine: 10, 15, 31, 45, 58, and 75 mM) on their loading efficiency to P-MSN and MSN-TA with various TA densities [P-MSN (0%), MSN-TA-1 (2%), TA-2 (5%), TA-3 (8%), TA-4 (12%) (v/v)] were investigated. FIG. 6 shows the adsorption profiles of Orange II adsorbed onto five different MSN samples. A general pattern was observed for all the four MSN-TA samples: the amount of Orange II molecules adsorbed onto the MSN-TAs increased as the concentration of Orange II was raised. This is probably due to a higher concentration of Orange II generating a larger gradient, which in turn facilitated the diffusion of Orange II molecules into the MSN nanochannels. It was noteworthy that the MSN-TA-2, MSN-TA-3, and MSN-TA-4 samples had very similar adsorption capacities for the low concentration of Orange II (0.25 mM), which indicated that these three types of MSN-TAs had more positively charged (TA) groups than the entering Orange II molecules and that this adsorption was therefore predominantly diffusion-dependent. At the higher Orange II concentration (0.75-2.25 mM), the amount of Orange II adsorbed onto MSN-TA increased with the increasing TA densities. That is, the amount loaded was: MSN-TA-4>MSN-TA-3>MSN-TA-2>MSN-TA-1>P-MSN). This suggested that the number of Orange II molecules was in excess of that of the positively charged molecules in the nanochannels and thus, a surface charge density-dependent adsorption profile was observed. The maximum adsorption of P-MSN, MSN-TA-1, MSN-TA-2, MSN-TA-3, and MSN-TA-4 samples for Orange II solution was 17.4, 70.9, 99.6, 132.9, and 167.8 mmol g$^{-1}$, respectively, following the order of the increase in TA (Table 1). A low loading of Orange II in P-MSN sample might have come from a higher electrostatic repulsion between the host and the guest at pH 6.8 (ζ-potential: −40.3 mV). As indicated in the previous experiments of nitrogen adsorption-desorption isotherms, the MSN-TA samples showed 33% decrease in surface area, 50% decrease in pore volume, and 5 Å decrease in pore size under the condition of the saturated adsorption. The decreases in these three parameters indicated that the channels were not fully occupied.

Figure 7:
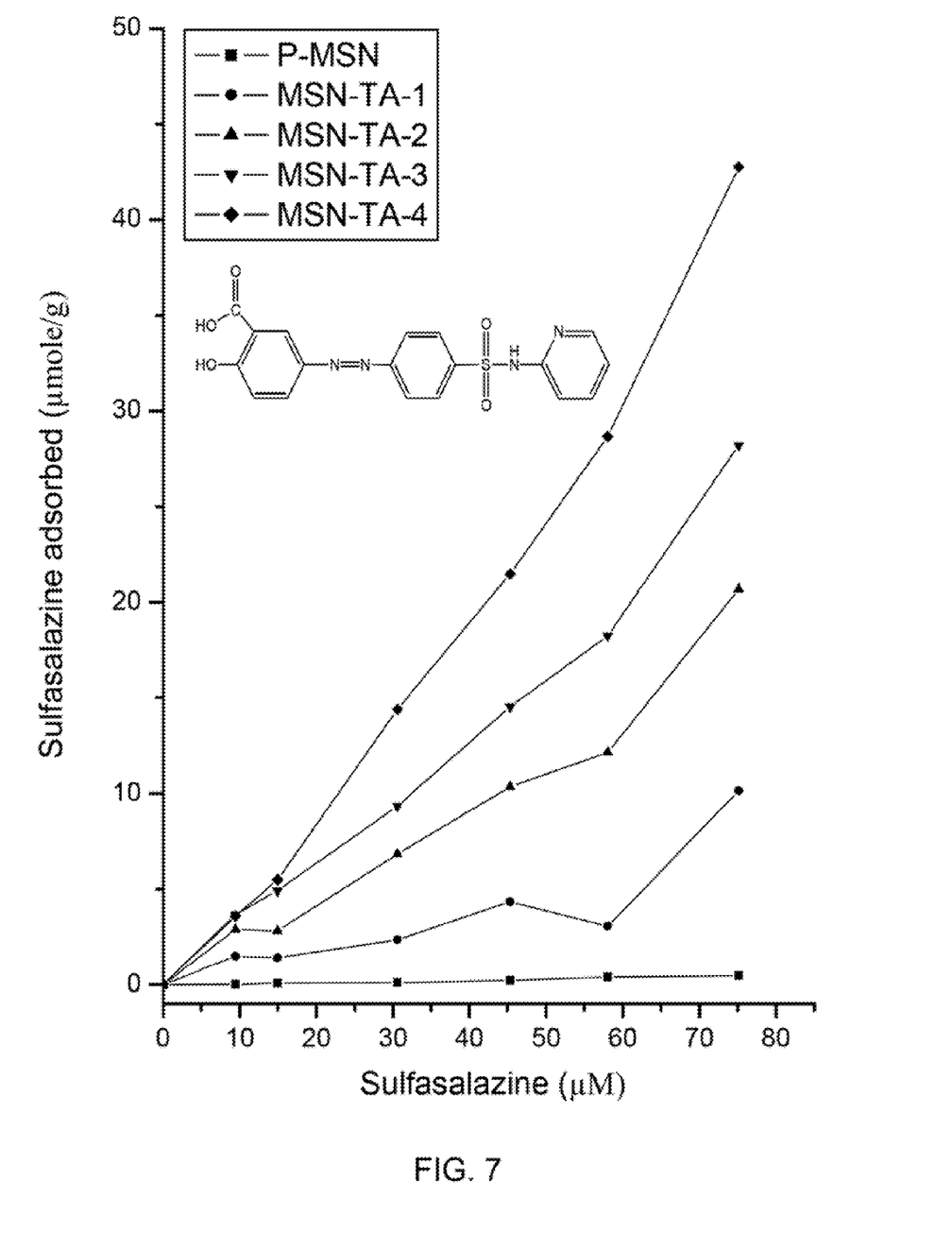
FIG. 7 shows sulfasalazine concentration versus adsorption curves for pure MSN (solid square), MSN-TA-1 (solid circle), MSN-TA-2 (solid triangle), MSN-TA-3 (solid, reverse triangle) and MSN-TA-4 (solid diamond).

FIG. 7 shows the adsorption curves of sulfasalazine onto P-MSN and MSN-TAs samples at different concentrations. The adsorbent profile that was similar to that of Orange II, and the loading of sulfasalazine molecules was enhanced with increasing sulfasalazine concentrations. In addition, MSN-TA-3 and -4 samples also showed the diffusion-dependent adsorption of sulfasalazine molecules at low concentration (10-15 mM). A similar surface charge density-dependent adsorption behavior at higher concentrations was observed. The maximum adsorption of P-MSN, MSN-TA-1, -2, MSN-TA-3, and MSN-TA-4 samples in sulfasalazine/H2O solution was 0.5, 10.1, 20.7, 28.2, and 42.8 mmol g$^{-1}$, respectively (Table 1). The maximum adsorption for sulfasalazine was lower than that of Orange II. The low loading efficiency might be because that sulfasalazine was more hydrophobic and showed less attraction to the hydrophilic nanochannels. In addition, the P-MSN sample not only exhibited the hydrophilic character but also had a low ζ-potential at pH 5.4 (ζ-potential: −32.5 mV). The strong electrostatic repulsion caused a low loading efficiency. To increase its loading, sulfasalazine was loaded onto MSN in DMSO. A higher concentration would facilitate the diffusion of sulfasalazine to enter hydrophilic nanochannels of MSN. The loading efficiency of sulfasalazine was higher in DMSO as compared to that in the aqueous solution. Table 1 shows the maximum adsorption of P-MSN, MSN-TA-1, MSN-TA-2, MSN-TA-3, and MSN-TA-4 in sulfasalazine/DMSO solution was 4.7, 59.6, 74.2, 87.5, and 103.1 mmol respectively.

Example 5

Effect of pH on Dye/Drug Adsorption

Figure 8:
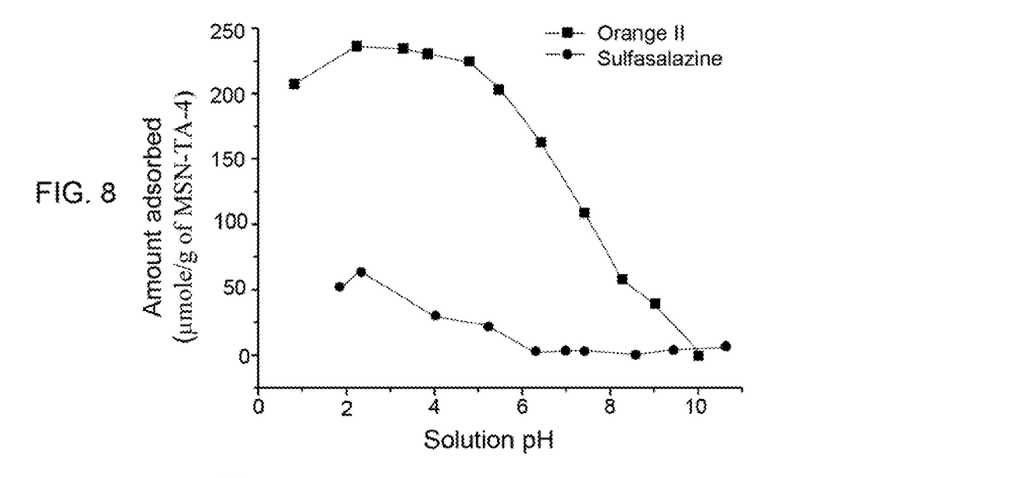
FIG. 8 shows pH versus adsorption curves for agents Orange II (solid square) and sulfasalazine (solid circle) adsorbed onto MSN-TA-4 samples.

Effects of environmental pH (from 1 to 10) on the adsorbed amount of Orange II (1.25 mM) and sulfasalazine (30.6 μM) molecules onto the MSN-TA-4 sample were investigated and the results shown in FIG. 8. Orange II and sulfasalazine have high loading efficiency at the pH ranging from 2 to 5. Because the pH value of PZC in the MSN-TA-4 sample was 6.73, the ζ-potential showed highly positive charge at the pH from 2 (+39.4 mV) to 5 (+29.2 mV). The high loading ability at this pH range was due to the strong electrostatic attraction. A slight decrease in the loading capability at the lower pH values (pH≦1.0) resulted from the protonation of the acidic groups in the dye/drug molecules (—SO3$^-$ to SO3H or —COO$^-$ to —COOH). Once the functional groups were protonated, the electrostatic attraction between the TA groups and the dye/drug molecules would decrease and cause a low loading efficiency. The decrease in the loading capability from pH 6 to 10 was resulted from the presence of unmodified silanol (Si—OH) groups on the surface of the MSN-TA sample. The silanol groups underwent deprotonation at the high pH value. The negative charges of Si—O$^-$ groups on the MSN-TA surface were produced, the z-potential therefore decreased from +13.3 mV (pH 6.0) to −38.0 mV (pH 10). The strong negative repulsion between the surface of the MSN and the loaded drug molecules caused a decrease in the adsorption at this pH range.

Example 6

Effects of the TA-Groups Density on the Release Rate

The major colonic drug-delivery systems developed during the past decade are based on formulation for time-dependent release, pH-sensitive polymer coatings, and prodrug systems. Formulations for time-dependent release are designed to delay the onset of drug release until the formulated drugs have reached the colon tissues. The precise control of this colon-specific release is not easily achieved due to variations in how long the formulated drugs may stay in the stomach and small intestine. The pH dependent release systems is based on the different pH values in various parts of the GI tract, which increases from pH 1.0-3.0 in the stomach, to pH 6.5-7.0 in the small intestine, and to pH 7.0-8.0 in the colon. Although successful passage through stomach can be expected, this design may result in an early release in the small intestine due to the insignificant pH variation between the small intestine and colon. The prodrug strategy has the advantage of producing active drug molecules by bacteria-catalyzed reaction in the colon (about $10^{12}$ CFU/mL). The existence of bacteria (about $10^4$ CFU/mL) in the stomach and small intestine, however, may lead to the production of active drug molecules in places other than the colon. Therefore, the present invention was designed as a nano-delivery vehicle that combines the advantages of pH-dependent release and prodrug systems. The prodrug compound sulfasalazine, which is commercially available, can be cleaved by colonic bacteria (Azoreductases) to produce 5-aminosalicylic acid (5-ASA), which acts as an active moiety for treating two major human chronic inflammatory bowel diseases (Crohn's disease and ulcerative colitis).

Figure 9:
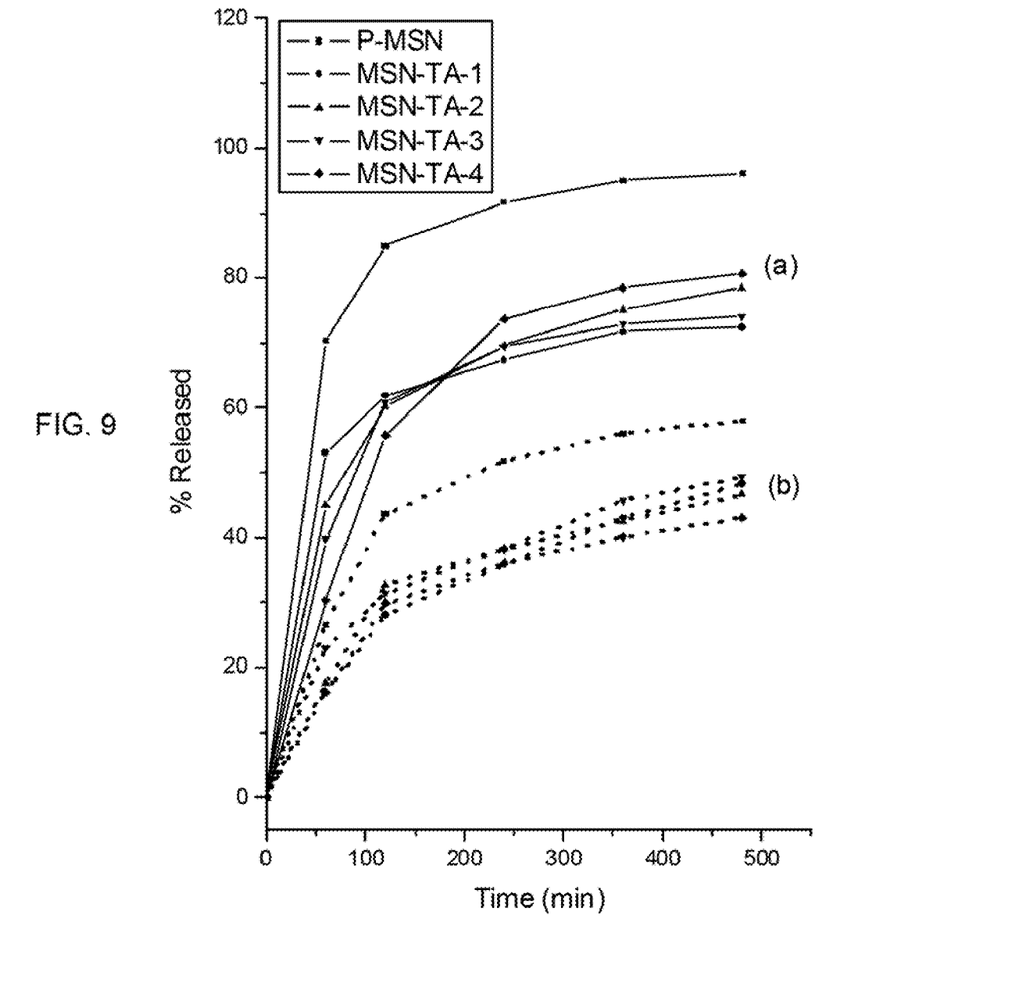
FIG. 9 shows time versus release curves for the agent Orange II at 37° C. in Ringer's (solid line, (a)) and 0.1 M HCl solution (dot line, (b)).

The release profile of loaded Orange II molecules in P-MSN and MSN-TAs samples was studied under simulated intestinal fluid (pH 7.4). The results are summarized in FIG. 9(a). MSN-TA samples with lower surface positive charge (MSN-TA-1) exhibited a higher initial burst release (53% of the loaded amount) within 60 min, and a slower release rate in the following 500 min (65% of the loaded amount). This initial burst release may be contributed from Orange II molecules that were adsorbed on the external surface outside of the MSN-TA nanochannels. On the contrary, MSN-TA-4 sample (with highest surface positive charge) showed only the release of 30% of loaded drugs in the initial 60 min; and then 80% within 500 min. The P-MSN sample, which was without any TA modification, showed a fast releasing profile within 120 min (85%). In addition, the release profile of MSN-TAs loaded with Orange II molecules in an environment similar to gastric fluid (pH 1.2) showed insignificant release not only in the initial burst release but also for the following 500 min. The release of Orange II molecules from MSN-TA samples may be dependent on two mechanisms: electrostatic repulsion (FIG. 11(c)) and ion exchange (FIG. 11(d). A large amount of Orange II molecules could be adsorbed in a weak acid environment pH (FIGS. 11(a) and 11(b)); they were released rapidly in pH 7.4 solutions. To facilitate the adsorption of negatively charged molecules, the MSN-TA samples were placed in solutions with pH value maintained in the range of 4-6, in such condition the unmodified silanol groups were protonated and uncharged and thus did not interfere the electrostatic attraction between the positively charged TA groups and the negatively charged dye/drug molecules (FIG. 11(b)). At physiological buffer (pH around 7.4), the silanol groups (Si—OH) in the MSN-TA surface would become deprotonated, and a strong electrostatic repulsion between the negative charges of MSN(SiO$^-$ groups) and the negative charge of dye/drug molecules (FIG. 11(c)) would be generated. Consequently, the pH value of 7.4 in the physiological buffer promoted the releasing rate of the anionic molecules. In the simulated gastric fluid (pH 1.2), the unmodified silanol groups in the MSN surface were fully protonated, so the MSN-TA surface predominantly carried positive charges (contributed from the TA groups). The electrostatic attraction between the positive charge of TA groups and negative dye/drug molecules in acidic condition caused a decrease in the release rate. The mechanism of slow release of Orange II in the simulated gastric fluid may be from the ion exchange (anionic dye/drug exchanged with Cl$^-$) and diffusion by the concentration gradient (FIG. 11(d)).

Figure 10:
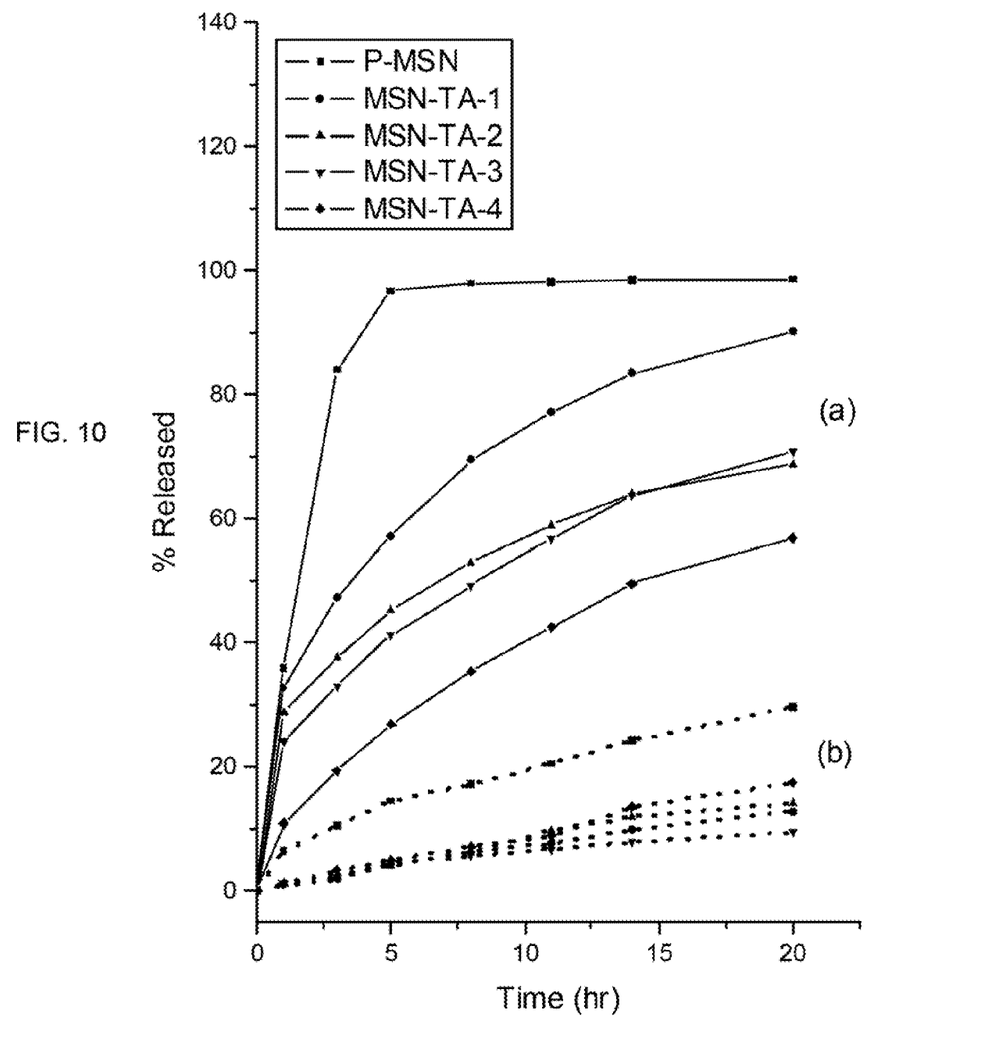
FIG. 10 shows time-versus release curves for the agent sulfasalazine at 37° C. in Ringer's (solid line, (a)) and 0.1 M HCl solution (dot line, (b)).

The release profiles of MSN-TAs-sulfasalazine samples in a simulated intestinal fluid (pH 7.4) are shown in FIG. 10(a). For the MSN-TA-1 sample, the highest initial burst release of 33% took place within 1 h, and 90% of the loaded sulfasalazine was slowly released within the following 20 h. MSN-TA-4 sample showed the lowest initial release rate in the initial 1 h (10%), and 57% was released within 20 h. From the release profiles of Orange II and sulfasalazine, one could effectively regulate the release rate by incorporating different amounts of TA groups inside the framework of MSN. In addition, the release rate of sulfasalazine in neutral pH was much slower when compared with that of Orange II molecules: A possible reason may be the hydrophobic nature of sulfasalazine molecules. Although the electrostatic repulsion will speed up the release rate of sulfasalazine molecules at a neutral pH, the hydrophilic environment of the releasing medium will prevent the sulfasalazine molecules from diffusing into the medium. FIG. 10b showed the release profiles of sulfasalazine in a simulated gastric fluid (pH 1.2). We observed that the MSN-TA samples were only trace release of sulfasalazine under pH 1.2, even though only 10% of sulfasalazine release in the 20 h of release period. The P-MSN loaded with Orange II or sulfasalazine showed a poor protection against the fast release either in physiological buffer (pH 7.4) or in simulated gastric fluid (pH 1.2). The drawbacks of P-MSN sample come from the low loading efficiency of the drug molecules (Table 1 and FIGS. 6 and 7) and the large leaching of the loading molecules under pH 1.2 of simulated gastric fluid, therefore the TA modified of MSN samples were indeed an ideal carrier for colonic targeted drug-delivery system.

It was indicated that the pore size of Si-MCM-41 would influence the release rate of the analgesic ibuprofen. Our experiments of nitrogen adsorption-desorption isotherms showed that the surface area and pore size were almost the same in P-MSN and MSN-TA samples (Table 1). The release rate of our MSN carriers was predominantly regulated by the surface charges in different pH values. This system exhibited sustained release property, though 10-20% of the loading molecules remained in the support for a long period. The residual dye/drug molecules may be occluded in the channels and therefore could not achieve the overall release. The electrostatic attraction between the dye/drug molecules and the MSN-TA surface was stronger than the hydrogen bonding (—NH2$^{\delta-}$-$^{\delta+}$HOOC—) and the weaker ionic attraction (NH3$^+$-$^-$OOC—). By the hydrophobic effect and electrostatic interaction, a prodrug molecule (sulfasalazine) targeting at colon tissue was protected and adsorbed inside the nanochannels of MSN-TA samples in the simulated gastric fluid, and this formulation of MSN-TA-sulfasalazine complex decreased both side effects and the degradation of prodrug molecules in the stomach and small intestine. To the best of our knowledge, this is the first report on the use of nanosized mesoporous silica to combine the pH-sensitive and prodrug strategies for oral drug delivery. It was expected that the combination of these two release mechanisms would be applicable to the colon-specific drug delivery following oral administration. Such a delivery system can reduce non-specific release during transportation and possible side effects in the stomach and small intestine.

In conclusion, a pH-responsive, controllable drug release system has been designed by incorporating positive charges into the framework of MSN so that anionic molecules can be efficiently adsorbed onto the surface of the nanochannels within charged MSN with minimal release under an acidic pH environment. At neutral pH because of the deprotonation of the surface silanol groups, which gives rise to a strong electrostatic repulsion, the release rate of the adsorbed drug molecules is increased. The amount of drug adsorbed and the release rate could be regulated by the control of the amounts of TA in the MSN. This controlled-release mechanism takes advantage of the changes in the pH and ionic strength in the physiological buffer.

The MSN-TA materials possess many advantages in pharmaceutical applications, including the control of particle size in the ~100 nm range, large surface areas, high pore volume, high loading of anionic drugs, which leads to a good control of the release rate. A series of MSN-TA samples with an average particle size of 100 nm, pore diameter of 2.7 nm, and different surface charges have great potential for utilizing the size-defined nanoparticles for targeted delivery and in vivo diagnostics. The storage capacity of the anionic molecules could be controlled either by varying the TA density in MSN or varying the concentration and pH value in the adsorption solution. It was demonstrated that a single step of solgel process could be used to synthesize a pH-triggered drug release system. The nanochannels of MSN-TA samples have the advantage of holding the drug molecules in acidic condition and protecting them from degradation in the stomach. Hence, this kind of the carrier could be designed as oral drug delivery system that improves site specificity and release kinetics to accommodate different therapeutic purposes.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:
1. A composition comprising:
a positively charged mesoporous silica nanoparticle (MSN), which comprises:
(a) a silica matrix, the entire substance of which comprises a plurality of silanol (Si—OH) and quaternary ammonium functional groups wherein the quaternary ammonium functional groups are from an organosilane quaternary ammonium compound comprising the formula:

wherein $R_1$, $R_2$, $R_3$, $R_4$, $R_5$, $R_6$, $R_7$ and $R_8$ are the same or different; $R_1$, $R_2$, and $R_3$ are, independently of each other, selected from the group consisting of alkyl and alkene groups; $R_4$, $R_5$, $R_6$, $R_7$ and $R_8$ are, independently of each other, selected from the group consisting of alkyl, ammonium, and hydrogen; n is an integer and $20 \geq n \geq 1$; and
(b) an array of pores and/or nanochannels in the matrix, each pore and/or nanochannel having a surface lining the wall thereof;
wherein the surface lining the wall of each pore and/or nanochannel comprises a plurality of silanol (Si—OH) and quaternary ammonium functional groups, and the positively charged MSN, in the absence of adsorption of a negatively charged compound, has a total pore volume of no smaller than 0.967 cm$^3$ g$^{-1}$.

2. The composition of claim 1, wherein the composition comprising the positively charged mesoporous silica nanoparticle (MSN) is prepared by a method comprising:
admixing a silicate precursor with a surfactant in the presence of a catalyst to form a crystal seed in a suspension;
adding an organosilane quaternary ammonium compound and an additional amount of the silicate precursor into the suspension to form a silica matrix; and
extracting the silica matrix with a solvent to remove the surfactant and thereby obtain the composition.

3. The composition of claim 1, wherein each pore and/or nanochannel comprises no oxysilyl functional groups (—O—Si) extending into the space inside the pore or nanochannel.

4. The composition of claim 1, wherein the positively charged MSN is characterized by having a nitrogen adsorption capability of greater than 500 cm$^3$ g$^{-1}$ at a relative pressure of between 0.9 and 1.0 (P/P$_o$).

5. The composition of claim 1, further comprising a plurality of negatively charged bioactive compound molecules, the negatively charged bioactive compound molecules being adsorbed onto the surfaces lining the pores and/or nanochannels.

6. The composition of claim 5, wherein the negatively charged bioactive compound molecules are attracted onto the quaternary ammonium functional groups on the surfaces lining the pores and/or nanochannels.

7. The composition of claim 5, wherein the entire silica matrix comprises a copolymer of a silicate precursor and an organosilane quaternary ammonium compound.

8. The composition of claim 5, wherein the plurality of silanol (Si—OH) functional groups on the surfaces lining the walls of the pores and/or nanochannels are provided by a silicate precursor that is incorporated into the matrix, and are free to deprotonate or to protonate, respectively, in a fluid having pH above or below the isolectric point (pI) of the positively charged MSN, 9. The composition of claim 5, wherein the bioactive compound is at least one selected from the group consisting of sulfa drugs, 5-aminosalicylic acid, aspirin, methotrexate, alendronate, ibuprofen, and amoxicillin.

10. The composition of claim 5, wherein the bioactive compound is an acidic, anionic compound.

11. A method of preparing a composition according to claim 1, comprising:
admixing a silicate precursor with a surfactant in the presence of a catalyst to crystal seed in a suspension;
adding an organosilane quaternary ammonium compound and an additional amount of the silicate precursor into the suspension to form a silica matrix; and
extracting the silica matrix with a solvent to remove the surfactant and thereby obtain the composition.

12. A method for preparing a colonic drug-sustained-release system comprising:
providing a composition according to claim 1; and
loading a plurality of negatively charged bioactive compound molecules into the pores and/or nanochannels to obtain the colonic drug-sustained-release system.

13. A method for enhancing the bioavailability of a negatively charged drug comprising the steps of:
providing a composition according to claim 1; and
loading a plurality of negatively charged drug molecules into the pores and/or nanochannels of the positively charged MSNs to obtain a composition comprising a MSN absorbed with the plurality of drug molecules and thereby enhancing the bioavailability of the negatively charged drug molecules.

14. The composition of claim 1, wherein the positively charged MSN is characterized by having a nitrogen adsorption capability of greater than 600 $cm^3$ $g^{-1}$ at a relative pressure of between 0.9 and 1.0 ($P/P_o$).

15. The composition of claim 14, further comprising a plurality of negatively charged bioactive compound molecules, the negatively charged bioactive compound molecules being adsorbed onto the surfaces lining the pores and/or nanochannels.

16. The composition of claim 1, wherein the positively charged MSN is characterized by having a nitrogen adsorption capability of greater than 1000 $cm^3$ $g^{-1}$ at a relative pressure of between 0.9 and 1.0 ($P/P_o$).

17. The composition of claim 1, wherein the positively charged MSN is characterized by having a nitrogen adsorption capability of greater than 1600 $cm^3$ $g^{-1}$ at a relative pressure of between 0.9 and 1.0 ($P/P_o$).

18. A composition comprising:
a positively charged mesoporous silica nanoparticle (MSN), which comprises:
(a) a silica matrix, the entire substance of which comprises a plurality of silanol (Si—OH) and quaternary ammonium functional groups wherein the quaternary ammonium functional groups are from an organosilane quaternary ammonium compound comprising the formula:

wherein $R_1$, $R_2$, $R_3$, $R_4$, $R_5$, $R_6$, $R_7$ and $R_8$ are the same or different; $R_1$, $R_2$, and $R_3$ are, independently of each other, selected from the group consisting of alkyl and alkene groups; $R_4$, $R_5$, $R_6$, $R_7$ and $R_8$ are, independently of each other, selected from the group consisting of alkyl, ammonium, and hydrogen; n is an integer and $20 \geq n \geq 1$; and
(b) an array of pores and/or nanochannels in the matrix, each pore and/or nanochannel having a surface lining the wall thereof;
wherein the surface lining the wall of each pore and/or nanochannel comprises a plurality of silanol (Si—OH) and quaternary ammonium functional groups, and the positively charged MSN, in the absence of adsorption of a negatively charged compound, has a total pore volume of no smaller than 0.967 $cm^3$ $g^{-1}$ and is characterized by having a nitrogen adsorption capability of greater than 400 $cm^3$ $g^{-1}$ at a relative pressure of between 0.9 and 1.0 ($P/P_o$).

19. The composition of claim 18, further comprising a plurality of negatively charged bioactive compound molecules, the negatively charged bioactive compound molecules being adsorbed onto the surfaces lining the pores and/or nanochannels.

* * * * *